US005207303A

United States Patent [19]
Oswalt et al.

[11] Patent Number: 5,207,303
[45] Date of Patent: May 4, 1993

[54] MEDICAL EMERGENCY CARRYING CASE

[76] Inventors: Brenda K. Oswalt; Robert A. Beeley, both of P.O. Box 55549, Houston, Tex. 77255

[21] Appl. No.: 730,206

[22] Filed: Jul. 15, 1991

[51] Int. Cl.⁵ .......................... A45G 3/00; B65D 30/00
[52] U.S. Cl. ..................... 190/108; 206/570; 383/37
[58] Field of Search ................. 383/37; 190/108; 150/145, 111

[56] References Cited

U.S. PATENT DOCUMENTS

| 504,840 | 9/1893 | Krick | 190/108 |
| 2,648,366 | 8/1953 | Higbee et al. | 190/108 X |
| 2,803,281 | 8/1957 | Sutton | 150/145 X |
| 5,007,470 | 4/1991 | Freeman | 150/145 X |
| 5,052,555 | 10/1991 | Harmon | 383/37 X |

FOREIGN PATENT DOCUMENTS 2059254 4/1981 United Kingdom .................. 383/37

Primary Examiner—William I. Price

[57] ABSTRACT

The invention relates to storage of medical emergency supplies in a medical carrying case. Windowed storage pouches are releasably attached to hinged fasteners located along or near the rims of the top and bottom compartments of the carrying case. The hinged attachment allows the storage pouches to be flipped from inside the carrying case to outside the carrying case while still attached. This arrangement allows for visible access at once to every item transported in the carrying case.

1 Claim, 3 Drawing Sheets

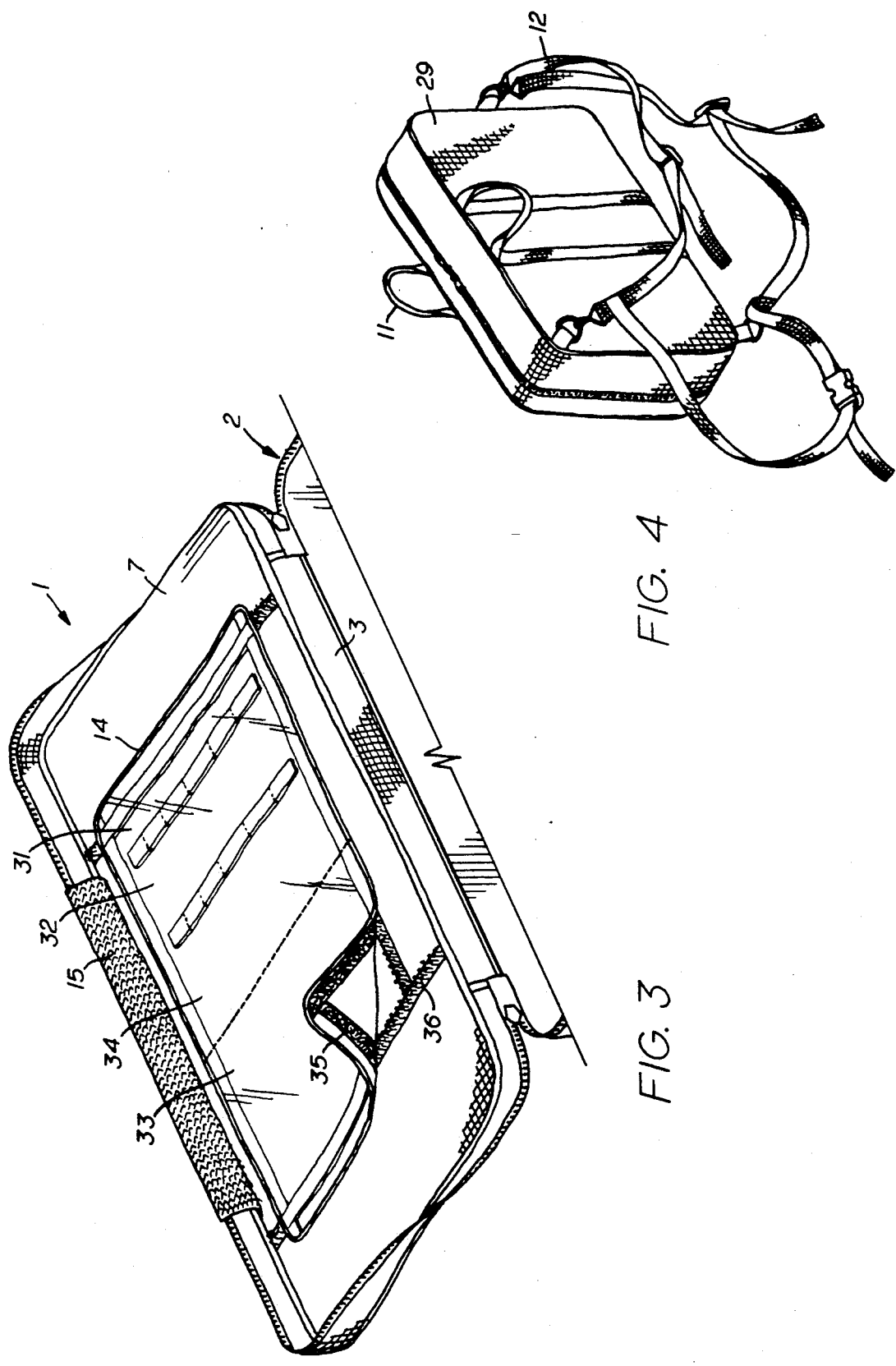

MEDICAL EMERGENCY CARRYING CASE

This invention is in the field of medical emergency kits.

BACKGROUND OF THE INVENTION

Many medical emergencies occur at places such as homes, offices and car accident sites, to which medical emergency personnel must travel with medical emergency supplies to render medical assistance. Some of these supplies are carried in medical emergency kits or cases. It is important that the medical emergency kits which are brought to medical emergency sites are lightweight enough to be quickly transported by people. It is important that such kits contain a complete line of medical emergency supplies so that any type of medical emergency victim may be adequately treated at the emergency site. In a medical emergency, rapid medical treatment can mean the difference between life and death of a victim. Therefore, it is also important in a medical emergency situation that all of the supplies in the kit be readily visible and that each of the personnel have ready access to the supplies.

A medical emergency portable pack is disclosed in U.S. Pat. No. 4,386,642 in which storage pouches are stored in the bottom of the pack. The pouches are separately releasably attachable to the bottom. The arrangement of pouches on the bottom of the pack does not permit the pouches to be removed from the bottom of the pack while still being attached to the pack, nor does it allow for the most efficient use of space in the pack.

A carrying case is disclosed in U.S. Pat. No. 3,381,782 in which partitioning members are used for generating compartments of various sizes and shapes in the base portion of the case. While such an arrangement permits reposition of the partitioning members to establish space sizes to fit a variety of items, it does not permit maximum visibility and access to every item stored in the case.

An emergency medical kit is disclosed in U.S. Pat. No. 4,169,550 which is essentially a backpack with a plurality of pockets and straps arranged to carry emergency medical equipment. Disadvantages of such a kit include the lack of simultaneous visible access to every item in the kit and limited access by more than one person at one time to items in the kit.

SUMMARY OF THE INVENTION

It is an object of this invention to allow for compact, efficient, visible and lightweight storage of a complete line of medical emergency supplies in a carrying case. Maximum storage in the carrying case is attained by layered placement of storage pouches which are releasably attached to hinges along the open edges of the carrying case. Additional storage is in the lid of the carrying case and in the bottom of the carrying case.

It is a further object of this invention to allow quick simultaneous visible access to every item in the carrying case. This is achieved by flipping the storage pouches out of the carrying case while they are still attached to the carrying case. In the flipped out position, clear windows in the pouches expose the contents of the pouches to view. With the storage pouches flipped outside the carrying case, all of the contents of the carrying case and the storage pouches are at once visible and readily accessible.

It is a further object of this invention that in the event of multiple casualties at the emergency scene the medical supplies may be used by more than one paramedic at locations remote from each other. To achieve this object, individual storage pouches are easily and readily detachable from the carrying case. Thus more than one paramedic may have ready access to the supplies.

Accordingly, these and other objects are achieved by this invention which is for a carrying case suitable for storing and transporting medical emergency supplies and which is arranged to provide maximum visibility of the stored items. Multi-compartment zippered and detachable pouches are attached to the inside of the carrying case and these pouches may be flipped out of the carrying case so that they are still attached to the carrying case but are no longer inside the carrying case. The pouches are transparent on at least one side so that when flipped outside the carrying case, though still attached to it, the items stored in the carrying case and stored in pouches releasably attached to the carrying case are in view and are readily and easily accessible.

BRIEF DESCRIPTION OF THE DRAWINGS

In the accompanying drawings, like numerals indicate like parts:

FIG. 3 is a perspective view of the window storage unit in the top compartment of the carrying case.

FIG. 4 is a perspective view of the carrying case in a closed condition.

DETAILED DESCRIPTION OF THE INVENTION

Figure 1:
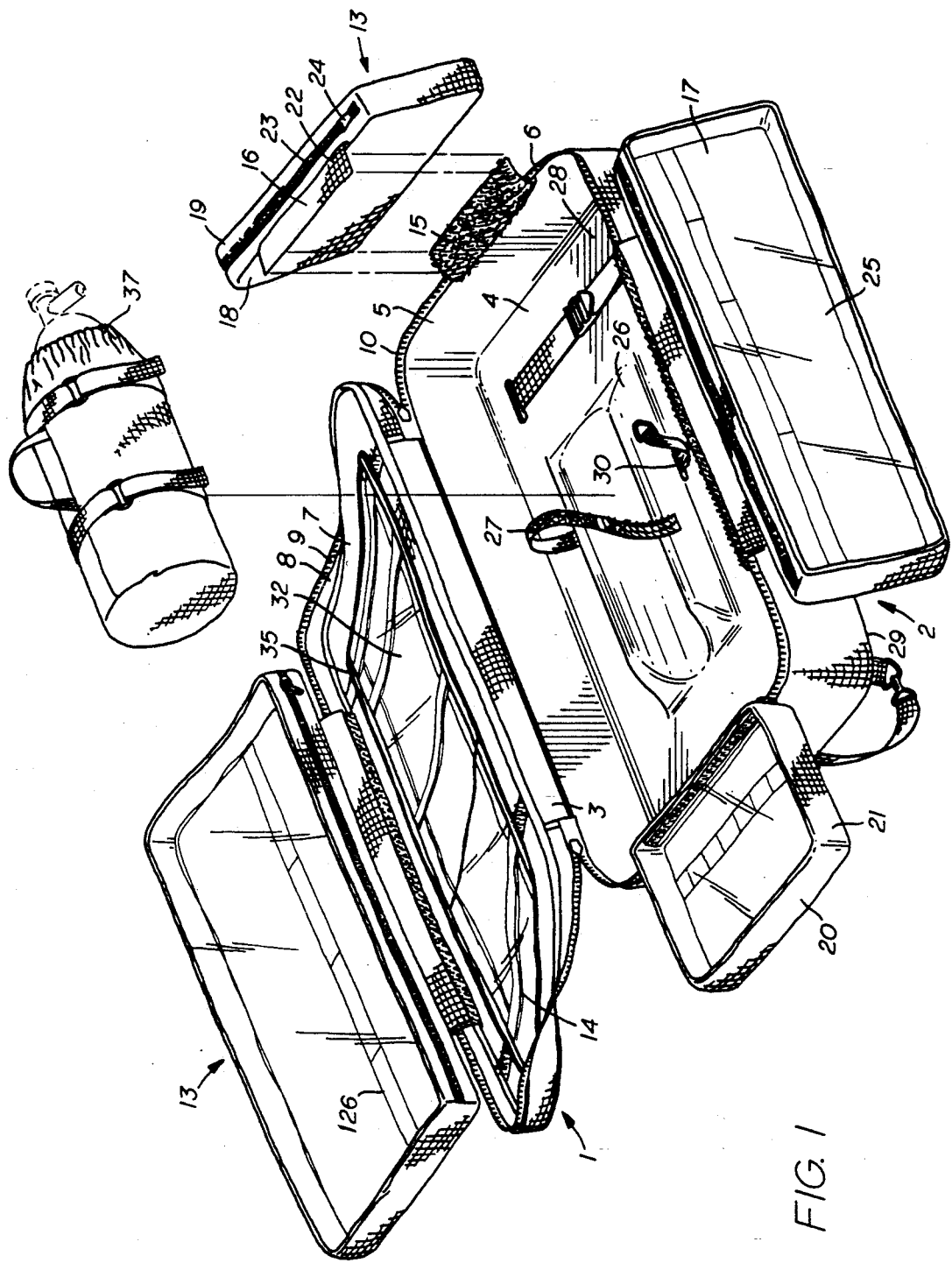
FIG. 1 is a perspective view of the carrying case in an open condition to show the attached storage pouches flipped out of the carrying case and to show a storage pouch detached from the carrying case.

Referring to FIG. 1, the exterior of the carrying case may be constructed of Cordura or other suitable wear resisting flexible material. The numeral 1 indicates the top compartment of the carrying case and the numeral 2 indicates the bottom compartment of the carrying case which are connected together along edge 3. The bottom compartment has a bottom panel 4 and sides 5 extending therefrom. The sides 5 terminate along rim 6. The top compartment has a top panel 7 and sides 8 extending therefrom. The sides 8 terminate along rim 9. Along the rims 6, 9 of the top compartment 1 and the bottom compartment 2 is a fastening means for fastening the rims together. In FIG. 1, the fastening means is zipper 10 which secures the compartments together when the carrying case is in a closed position. There may be other suitable fasteners such as snaps for securing the carrying case in a closed condition.

As shown in FIG. 1, storage of medical emergency supplies in the carrying case is achieved by a plurality of detachable storage pouches 13 as well as a window storage unit 14 in the top compartment 1 and storage capacity in the bottom panel 4 in the bottom compartment 2.

As shown in FIG. 1, the storage pouches 13 are attached to the carrying case by strips of VELCRO 15. Other suitable fasteners could include zippers or snaps, but VELCRO is preferred because it allows quick attachability and releasability which is important in medical emergencies. The VELCRO fasteners 15 are affixed to the carrying case along segments of the rims 6, 9 of the top 1 and bottom 2 compartments. Alternatively, the VELCRO fasteners 15 could be attached near the rims 6, 9. Only one edge of the VELCRO is attached to the carrying case so that the VELCRO fastener 15 is movable as a flap or hinge.

Attached to the storage pouch 13 is the mating VELCRO fastener 16. One edge of the mating VELCRO fastener 16 is stitched within a seam of the storage pouch 13, so that the mating VELCRO fastener 16 is movable as a flap or hinge. The carrying case's hinged VELCRO fastener 15 may be releasably attached to the storage pouch's hinged mating VELCRO fastener 16 so that the storage pouch 13 is movable in an arc around the point of hinged attachment to the carrying case. In other words, the storage pouch 13 may be flipped from inside a compartment 1, 2 of the carrying case over the rim 6, 9 of the compartment 1, 2 to outside the compartment 1, 2 of the carrying case while remaining attached to the carrying case.

The storage pouch 13 can be of varying sizes, limited in length only by the location along the rims 6, 9 of the compartments 1, 2 where it is attached to the hinged VELCRO fastener 15. The storage pouch 13 may be composed of water resistant nylon material or other suitable material. The preferred shape of the storage pouch 13 is a rectangular box structure having a broad front 17 and a broad back 18 and a narrow top 19 and a narrow bottom 20 and two narrow sides 21. However, the storage pouch 13 may be of other shapes and fall within the scope of this invention. The hinged mating VELCRO fastener 16 is located at the junction 22 of the top 19 and the back 18 of the storage pouch 13.

Articles may be placed inside the storage pouch 13 through an aperture 23. The aperture 23 is located along the length of the top side 19 of the storage pouch 13. There is a zipper 24 for opening and securely closing the aperture 23. Other fasteners such as VELCRO or snaps could be used instead of a zipper.

It is desirable to see inside the storage pouch 13, especially in a medical emergency situation, and the window 25 located on the front side 17 of the storage pouch 13 allows visibility of the articles contained therein. It is preferred that the window 25 is a clear transparent non-yellowing non-cracking flexible material, although window 25 could be made of any transparent material. When the storage pouch 13 is inside the carrying case, as in FIG. 2, the window 25 is not exposed to view. When the storage pouch 13 is flipped outside the carrying case, as in FIG. 1, the window 25 is in view so that the contents of the storage pouch 13 are visible. Located along the length of the interior of the back side 18 of the storage pouch 13 is a strip of elastic material 126 which is attached at intervals so that articles may be secured between the unattached sections of the elastic material and the interior of the back side 18 of the storage pouch 13.

To provide the bottom compartment 2 of the carrying case with rigidity, and protection for items stored there, the interior component 28 of the bottom compartment 2 is comprised of a sturdy material such as plastic, snugly encased exteriorly by the fabric comprising the exterior of the carrying case.

The sturdy interior bottom panel 4 of the bottom compartment 2 has a molded configuration 26 suitable for storing an oxygen canister 37, as shown in FIG. 1.

Securing the canister to the molded configuration 26 is a strap 27 which is in part contained under the molded configuration 26 between the interior 28 of the bottom compartment 2, and the exterior 29 of the bottom compartment 2. The strap 27 is threaded through slits 30 in the sides of the molded configuration 26 so as to be available for securing the article stored in the molded configuration 26.

As shown in FIG. 3, the interior of the top panel 7 of the top compartment 1 of the carrying case has pockets 31 for storage. Covering the interior of the top panel 7 is a protective window 32 which is a clear transparent non-yellowing non-cracking flexible material. Near the midline of the window 32 in a direction perpendicular to the edge 3 along which the top compartment 1 is connected to the bottom compartment 2, the window 32 is non-releasably attached to the interior of the top panel 7 of the top compartment 1, thereby forming two window flaps 33, 34. To access the articles in the storage pockets 31, the window flaps 33, 34 are releasably attached to the top panel 7 along their perimeters by mating strips of VELCRO 35, 36.

Figure 2:
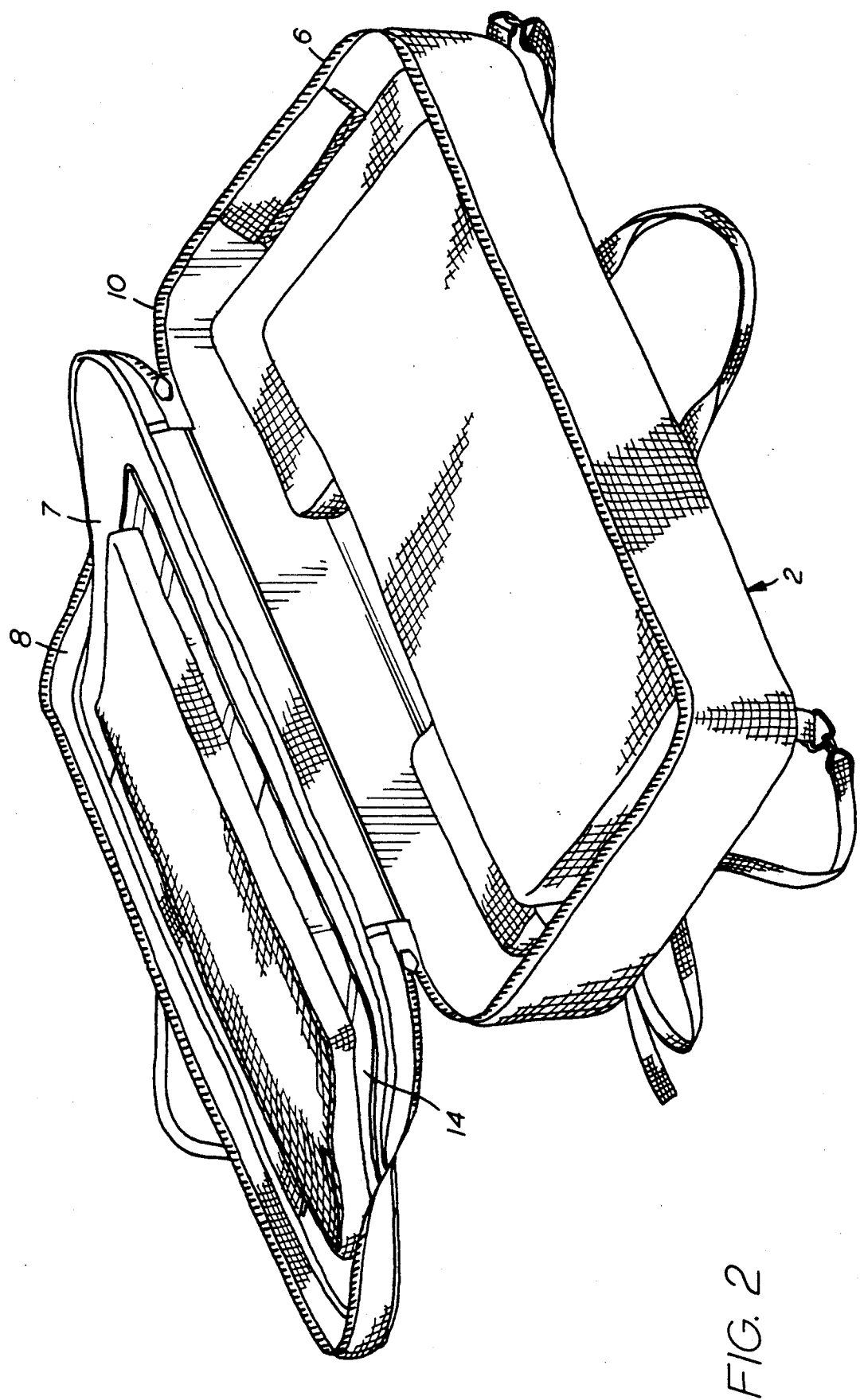
FIG. 2 is a perspective view of the carrying case in an open condition to show a combination of attached storage pouches flipped inside of the carrying case in an arrangement that will allow for convenient closure of the carrying case.

When responding to an emergency call, the closed carrying case may be conveniently carried by use of the carrying handles 11 or the harness strap 12 (see FIG. 4) which is suitable for strapping to the back or shoulder of a person. As shown in FIG. 2, the storage pouches 13 are attached to the VELCRO fasteners 15 on the carrying case and are layered inside the carrying case for maximum storage.

Upon arrival at the emergency site, the carrying case is opened and the storage pouches 13 are flipped outside the carrying case so that every item in the storage pouches 13 and in the top 1 and bottom 2 compartments are visible and readily accessible to one or more medical personnel. The storage pouches 13 may be quickly detached and reattached to the carrying case. The window 32 over the storage unit 14 in the top compartment 1 may be quickly partially detached for access to the articles therein.

Utensils such as forceps, tongs, scissors, scalpels and ring cutters would be stored in the pockets 31 of the top compartment 1. The storage pouches 13 would include supplies such as a poison antidote kit, an oxygen face mask, burn dressings, bandages, cold compress packs, a tourniquet, ammonia inhalants, eye pads, a cervical collar, an obstetric kit, a syringe, tape, gauze and a stethoscope. In the molded configuration 26 of the bottom compartment 2 would be stored an oxygen canister. All of these items, and more, can be compactly and efficiently stored in the medical emergency carrying case described herein.

What is claimed is:

1. A carrying case comprising:
    a rectangular top compartment having a panel with four sides extending therefrom with each of the four sides terminating in a rim;
    a rectangular bottom compartment having a panel with four sides extending therefrom with each of the four sides terminating in a rim, with one side of the top compartment hingedly joined to the corresponding side of the bottom compartment so that the case may be opened and closed;
    a zipper for fastening the top compartment to the bottom compartment when the case is closed;
    a first fastener attached internally along the rim of the side of the top compartment opposite the side of the top compartment hingedly joined to the bottom compartment, said first fastener being a four edged strip of VELCRO stitched as a flap to said rim with the coarse side of the VELCRO facing said side;

a second fastener attached internally along the rim of the side of the bottom compartment opposite the side of the bottom compartment hingedly joined to the top compartment, said second fastener being a four edged strip of VELCRO stitched as a flap to said rim with the coarse side of the VELCRO facing said side;

a third fastener attached internally along the rim of the side of the bottom compartment adjacent to the side on which is located the second fastener, said third fastener being a four edged strip of VELCRO stitched as a flap to said rim with the coarse side of the VELCRO facing said side;

a fourth fastener attached internally along the rim of the side of the bottom compartment opposite the side on which is located the third fastener, said fourth fastener being a four edged strip of VELCRO stitched as a flap to said rim with the coarse side of the VELCRO facing said side;

a first storage pouch having a plurality of sides, a zippered aperture, an elastic tab inside the pouch, and a transparent window through which the contents of the storage pouch are readily visible;

a fifth fastener attached to a seam of the first storage pouch, said fastener being a four edged strip of VELCRO corresponding in length to the first fastener and stitched as a flap to said pouch with the coarse side of the VELCRO facing away from the transparent window of said pouch;

a second storage pouch having a plurality of sides, a zippered aperture, an elastic tab inside the pouch, and a transparent window through which the contents of the storage pouch are readily visible;

a sixth fastener attached to a seam of the second storage pouch, said fastener being a four edged strip of VELCRO corresponding in length to the second fastener and stitched as a flap to said pouch with the coarse side of the VELCRO facing away from the transparent window of said pouch;

a third storage pouch having a plurality of sides, a zippered aperture, an elastic tab inside the pouch, and a transparent window through which the contents of the storage pouch are readily visible;

a seventh fastener attached to a seam of the third storage pouch, said fastener being a four edged strip of VELCRO corresponding in length to the third fastener and stitched as a flap to said pouch with the coarse side of the VELCRO facing away from the transparent window of said pouch;

a fourth storage pouch having a plurality of sides, a zippered aperture, an elastic tab inside the pouch, and a transparent window through which the contents of the storage pouch are readily visible;

an eighth fastener attached to a seam of the fourth storage pouch, said fastener being a four edged strip of VELCRO corresponding in length to the fourth fastener and stitched as a flap to said pouch with the coarse side of the VELCRO facing away from the transparent window of said pouch;

a liner interiorly covering the panel of the bottom compartment, said liner being composed of rigid plastic and having a molded configuration for storing an oxygen canister, and having a strap for securing an oxygen canister to the liner;

a removable sleeve in which an oxygen canister may be positioned;

a storage unit in the top compartment, said unit having pockets, a plurality of elastic tabs, a flexible transparent rectangular cover permanently attached to the interior of the top compartment near the midline of the cover forming two flaps and having a VELCRO strip attached along the perimeter of the cover for releasably attaching the two flaps of the cover to the interior of the top compartment, and a VELCRO strip attached to the interior of the top compartment for mating to the VELCRO strip of the cover;

a backpack harness attached exteriorly to the bottom compartment, said harness being convertible to a shoulder strap; and two exterior carry handles.

* * * * *